(12) United States Patent
Shimamura (10) Patent No.: US 11,903,603 B2
(45) Date of Patent: Feb. 20, 2024

(54) ULTRASONIC TRANSDUCER

(71) Applicant: OLYMPUS CORPORATION, Hachioji (JP)

(72) Inventor: Yukihiko Shimamura, Yoshikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 1349 days.

(21) Appl. No.: 16/382,421

(22) Filed: Apr. 12, 2019

(65) Prior Publication Data

US 2019/0231383 A1    Aug. 1, 2019

Related U.S. Application Data (63) Continuation of application No. PCT/JP2016/080568, filed on Oct. 14, 2016.

(51) Int. Cl.
*A61B 17/32* (2006.01)
*G10K 11/02* (2006.01)
(Continued)

(52) U.S. Cl.
CPC ...... *A61B 17/320068* (2013.01); *A61B 18/00* (2013.01); *B06B 1/0611* (2013.01);
(Continued)

(58) Field of Classification Search
CPC ............... B06B 1/0611; B06B 2201/76; A61B 2017/32009; A61B 2017/320094;
(Continued)

(56) References Cited

U.S. PATENT DOCUMENTS 7,285,895 B2 * 10/2007 Beaupre ............... B06B 1/0611
310/323.12
8,152,825 B2 *  4/2012 Madan ................. A61B 8/4455
310/311
(Continued)

FOREIGN PATENT DOCUMENTS

JP    2015-521897 A    8/2015
WO    2014/004097 A1   1/2014
(Continued)

OTHER PUBLICATIONS

Jan. 10, 2017 International Search Report issued in International Patent Application No. PCT/JP2016/080568.

*Primary Examiner* — J. San Martin
(74) *Attorney, Agent, or Firm* — Oliff PLC (57) ABSTRACT

An ultrasound transducer includes: a drive unit including a piezoelectric device; a proximal end block; and a distal end block. The distal end block includes a first portion, a supported portion, a second portion, and a third portion. The distal end block is configured such that a position of a boundary between the second portion and the third portion corresponds to or substantially corresponds to an antinode of the ultrasonic vibration while the piezoelectric device generates the ultrasonic vibration, and the ultrasonic vibration is being propagated to the proximal end block, the first portion, the second portion, and the third portion. A resonance frequency of the ultrasonic vibration differs according to a position of the boundary between the second portion and the third portion under a condition that a distance from the supported portion to a distal end of the third portion along the longitudinal axis is constant.

21 Claims, 7 Drawing Sheets

(51) Int. Cl.
    *B06B 1/06*     (2006.01)
    *H04R 17/10*     (2006.01)
    *A61B 18/00*     (2006.01)

(52) U.S. Cl.
    CPC ............ *G10K 11/02* (2013.01); *H04R 17/10* (2013.01); *A61B 2017/32009* (2017.08); *A61B 2017/320094* (2017.08); *B06B 2201/76* (2013.01)

(58) Field of Classification Search
    CPC ........ A61B 18/00; A61B 17/320068; H04R 17/00; G10K 11/02
    See application file for complete search history.

(56) References Cited

U.S. PATENT DOCUMENTS

| | | | |
|---|---|---|---|
| 9,801,649 B2 * | 10/2017 | Akagane | ............ A61B 18/1442 |
| 2009/0275864 A1 | 11/2009 | Hirai | |
| 2014/0005705 A1 | 1/2014 | Weir et al. | |
| 2014/0358043 A1 | 12/2014 | Akagane | |
| 2015/0011888 A1 | 1/2015 | Akagane | |
| 2016/0199881 A1 | 7/2016 | Akagane | |
| 2017/0274226 A1 | 9/2017 | Akagane | |
| 2017/0274420 A1 * | 9/2017 | Toda | ................. H04R 17/10 |
| 2018/0297079 A1 * | 10/2018 | Toda | ................. A61B 18/00 |
| 2019/0239916 A1 * | 8/2019 | Yoshimine | ............ H04R 17/10 |

FOREIGN PATENT DOCUMENTS

| | | | |
|---|---|---|---|
| WO | 2014/024550 A1 | 2/2014 | |
| WO | 2014/065406 A1 | 5/2014 | |
| WO | 2015/072326 A1 | 5/2015 | |
| WO | 2016/147769 A1 | 9/2016 | |
| WO | WO-2018070044 A1 * | 4/2018 | ............ A61B 17/29 |

\* cited by examiner

ULTRASONIC TRANSDUCER

This application is a continuation of International Application No. PCT/JP2016/080568, filed on Oct. 14, 2016, the entire contents of which are incorporated herein by reference.

BACKGROUND

The present disclosure relates to an ultrasound transducer.

For ultrasound treatment tools, such as the one disclosed in US2009/275864A1, it is desirable for a vibrator including an ultrasound transducer and a rod member to vibrate at or as close as possible to a predetermined resonance frequency, from the viewpoint of treatment performance. Furthermore, it is desirable for a single ultrasound transducer to vibrate at or as close as possible to the predetermined resonance frequency of ultrasonic vibrations generated by the piezoelectric device to reduce energy loss. Accordingly, it is necessary to form an ultrasound transducer that vibrates at the predetermined resonance frequency even with a single unit (a smallest component unit of the ultrasound transducer, and a derived unit of a natural number multiple of a half wavelength of vibration), according to physical properties and the like of respective parts constituting the ultrasound transducer, such as the piezoelectric device, the distal end block, the proximal end block. Thus, the resonance frequency of vibration with a single unit of the ultrasound transducer should match or approximately match with an input current from a driving power source or a frequency of an n input voltage, and the resonance frequency of vibration with a single unit of the rod member.

The resonance frequency of vibration with a single unit of the ultrasound transducer is influenced by physical properties (properties of material), such as rigidity (Young's modulus) of a material constituting the ultrasound transducer. The properties of material vary depending on a manufacturer that provides the material, or vary among rods even from the same manufacturer. To adjust the resonance frequency of vibration by a single unit of the ultrasound transducer, it is conceivable that a length along a longitudinal axis of the distal end block of the ultrasound transducer is changed. This adjustment can be performed easily.

However, to change the length along the longitudinal axis of the distal end block, it becomes necessary to change dimensions of the other parts constituting the ultrasound treatment tool also. Particularly, the dimensions of a grip unit constituted of a handle, the rod member, and the like are designed according to the length along the longitudinal axis of the distal end block. As described, changing sizes of one part constituting ultrasound treatment tools has a large influence over a structure of an entire product.

SUMMARY

An ultrasound transducer according to one aspect of the present disclosure includes: a drive unit including a piezoelectric device that generates ultrasonic vibration by supply of electric energy, along a longitudinal axis; a proximal end block that is arranged on a first end side of the drive unit along the longitudinal axis; and a distal end block that is arranged on a second end side opposite to the first end side of the drive unit, wherein the distal end block includes, sequentially from the second end side of the drive unit along the longitudinal axis: a first portion adjacent to the piezoelectric device; a supported portion that is arranged in the first portion; a second portion that is arranged continuously to the first portion; and a third portion that is arranged continuously to the second portion, and that is structured such that a cross-sectional area of a virtual plane perpendicular to the longitudinal axis differ from a cross-sectional area of the second portion, the distal end block is configured such that a position of a boundary between the second portion and the third portion corresponds to or substantially corresponds to an antinode of the ultrasonic vibration in a state in which the piezoelectric device generates the ultrasonic vibration, and the ultrasonic vibration is being propagated to the proximal end block, the first portion, the second portion, and the third portion, a resonance frequency of the ultrasonic vibration differs according to a position of the boundary between the second portion and the third portion under a condition that a distance from the supported portion to a distal end of the third portion along the longitudinal axis is constant.

The above and other features, advantages and technical and industrial significance of this disclosure will be better understood by reading the following detailed description of presently preferred embodiments of the disclosure, when considered in connection with the accompanying drawings.

DETAILED DESCRIPTION

An ultrasound transducer 20 according to an exemplary embodiment is described.

Figure 1:
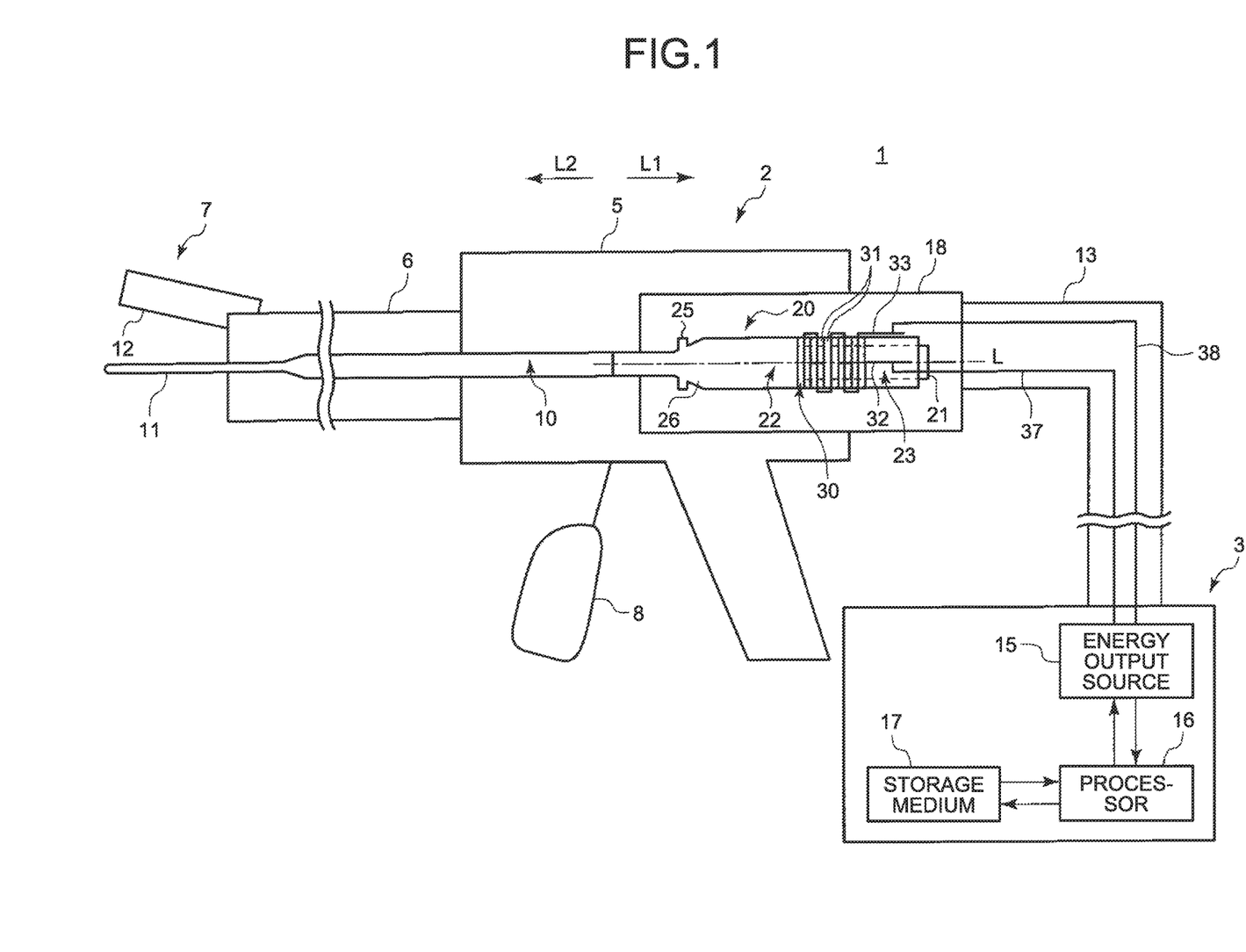
FIG. 1 is a schematic diagram of a treatment system in which an ultrasound transducer according to an exemplary embodiment is used.

FIG. 1 is a schematic diagram of a treatment system 1 in which the ultrasound transducer 20 as an example is used.

As illustrated in FIG. 1, the treatment system 1 includes an ultrasound treatment tool 2 and an energy control device 3. The ultrasound treatment tool 2 includes a housing 5 and a shaft 6 that is attached to the housing 5. The shaft 6 extends substantially straight. In the ultrasound treatment tool 2, a side on which the housing 5 is positioned relative to the shaft 6 is regarded as a proximal end side (arrow L1 side), and the opposite side to the proximal end side is regarded as a distal end side (arrow L2 side). Accordingly, the shaft 6 is attached to the housing 5 from the distal end side. Moreover, in the ultrasound treatment tool 2, at a portion on the distal end side relative to the shaft 6, an end effector 7 is provided.

To the housing 5, a handle 8 is pivotably attached. As the handle 8 pivots about the housing 5, the handle 8 opens or closes with respect to the housing 5. Furthermore, a rod member (probe) 10 is inserted through the shaft 6. The rod member 10 is made from a material having a high vibration transferability, such as titanium alloy. The rod member 10 passes through the inside of the shaft 6 from the inside of the housing 5, and extends toward the distal end side. The rod member 10 includes a rod protruding portion 11 that protrudes toward the distal end side from a distal end of the shaft 6. Moreover, to a distal end portion of the shaft 6, a jaw 12 is pivotably attached. The jaw 12 and the handle 8 are connected through a movable member (not shown) that extends through the inside of the shaft 6. As the handle 8 is opened or closed with respect to the housing 5, the movable member moves toward the proximal end side or the distal end side. Thus, the jaw 12 pivots about the shaft 6, and space between the jaw 12 and the rod protruding portion 11 is opened or closed. The end effector 7 is formed with the rod protruding portion 11 and the jaw 12. By holding a subject of treatment, such as a living tissue, between the jaw 12 and the rod protruding portion 11, the subject of treatment is treated.

In an implementation example, a rotating knob (not shown) that is a rotatable operating member is attached to the housing 5, and the rotating knob is rotatable about a center axis of the shaft 6 with respect to the housing 5. In this case, by rotating the rotating knob, the shaft 6, the end effector 7, and the rod member 10 rotate about the center axis of the shaft 6 together with respect to the housing 5. Moreover, in an implementation example, the jaw 12 is not provided, and the end effector 7 is constituted only of the rod protruding portion 11. In this case, the handle 8 and the movable member described above are not provided. Furthermore, in this case, the rod protruding portion 11 includes a hook shape, a spatula shape, a blade shape, or the like.

The ultrasound transducer 20 is connected to the rod member 10 from the proximal end side inside the housing 5. The ultrasound transducer 20 is housed inside a transducer case 18, and is supported by the transducer case 18. By attaching the transducer case 18 to the housing 5 from the proximal end side, the ultrasound transducer 20 is connected to the rod member 10. A distal end of the ultrasound transducer 20 is connected directly to a proximal end of the rod member 10. Furthermore, one end of a cable 13 is connected to the transducer case 18. The other end of the cable 13 is detachably connected to the energy control device 3.

In an implementation example, the transducer case 18 is not provided. In this case, the ultrasound transducer 20 is supported by the housing 5, and one end of the cable 13 is connected to the housing 5. Moreover, in the implementation example in which the rotating knob is provided, by rotating the rotating knob, the ultrasound transducer 20 rotates about the center axis of the shaft 6 with respect to the housing 5 together with the shaft 6, the end effector 7, and the rod member 10.

Next, a configuration of the ultrasound transducer 20 is described.

The ultrasound transducer 20 includes a bolt (shaft) 21 that extends along a longitudinal axis L. One end in a direction along the longitudinal axis L corresponds to the proximal end side (arrow L1 side), and the other side in a direction along the longitudinal axis L corresponds to the distal end side (arrow L2 side). The bolt 21 extends straight along the longitudinal axis L from the proximal end to the distal end.

In the ultrasound transducer 20, the distal end of the bolt 21 is connected to a distal end block 22 to be a vibrating member. The distal end block 22 is also referred to as front mass. The distal end block 22 is unified with the bolt 21. The distal end block 22 is provided on the distal end side opposite to the proximal end side of a drive unit 30 described later along the longitudinal axis L. The distal end block 22 and the bolt 21 are made from, for example, titanium alloy, aluminum alloy, stainless steel (SUS), or the like. Note that the distal end block 22 may be made from the same material as the bolt 21, or may be made from a material different from that of the bolt 21. Moreover, the distal end block 22 forms the distal end of the ultrasound transducer 20, and is connected to the rod member 10. The distal end block 22 includes a supported portion 25, such as a flange, supported by the transducer case 18 or the housing 5, and a horn 26 having a cross-sectional area substantially perpendicular to the longitudinal axis L that decreases toward the distal end side. Positions at which the supported portion 25 and the horn 26 are formed in the distal end block 22 are described later.

In the ultrasound transducer 20, the proximal end portion of the bolt 21 is connected to a proximal end block 23 to be a vibrating member. The proximal end block 23 can be referred to as back mass also. The proximal end block 23 is provided on a proximal end side of the drive unit 30 described later along the longitudinal axis L. The proximal end block 23 is formed in a ring shape covering an outer periphery of the bolt 21. On the outer periphery of the bolt 21 at the proximal end portion, a male screw portion not shown is formed as a first engaging unit. Moreover, on an internal periphery of the proximal end block 23, a female screw portion not shown is formed as a second engaging unit that engages with the first engaging unit. The male screw portion extends from the proximal end of the bolt 21 toward the distal end side, and the female screw portion extends from the proximal end of the proximal end block 23 toward the distal end side. As the male screw portion and the female screw portion engage with each other, that is, screwed, the proximal end block 23 is fastened to outer periphery of the bolt 21. Therefore, the proximal end block 23 is a fastening member that is fastened onto the outer periphery of the bolt 21.

The proximal end block 23 is made from, for example, titanium alloy, aluminum alloy, SUS, or the like. The proximal end block 23 may be formed from the same material as the distal end block 22, or may be made from a material different from that of the distal end block 22. Furthermore, a position of the proximal end of the proximal end block 23 substantially corresponds to a position of the proximal end of the bolt 21 in a direction along the longitudinal axis L, and the proximal end of the proximal end block 23 and the proximal end of the bolt 21 from the proximal end of the ultrasound transducer 20.

On the outer periphery of the bolt 21, the drive unit 30 to be an excitation member is attached. The drive unit 30 is sandwiched between the distal end block 22 and the proximal end block 23 in the direction along the longitudinal axis L. Furthermore, the drive unit 30 is pushed toward the distal end block 22 by the proximal end block 23. The drive unit 30 includes one or more piezoelectric devices 31 that generate ultrasonic vibrations along the longitudinal axis L by supply of electric energy. The drive unit 30 includes, for example, 10 pieces of the piezoelectric devices 31. The piezoelectric device 31 is made from, for example, piezoelectric ceramic or the like. The piezoelectric device 31 converts electric energy into vibrational energy. Each of the piezoelectric devices 31 is formed in a ring shape, and the bolt 21 is inserted through each of the piezoelectric device 31. At least one unit of the piezoelectric device 31 may be provided.

Moreover, the drive unit 30 includes plural ring-shaped electrode members 32 and 33 made from a conductive material, such as metal. The plural electrode members 32 are joined together. The plural electrode members 33 are joined together. To the electrode member 32, one end of an electric wiring 37 is connected. Moreover, to the electrode member 33, one end of an electric wiring 38 is connected. Furthermore, the number of the electrode members 32 and 33 is determined corresponding to the number of the piezoelectric devices 31, and in any case, it is configured such that each of the piezoelectric devices 31 is sandwiched between a corresponding one of the electrode member 32 and a corresponding one of the electrode member 33. As the ultrasound transducer 20 is formed as described above, the ultrasound transducer 20 in the present embodiment is a bolt-clamped Langevin-type transducer.

Next, a configuration of the energy control device 3 is described.

The energy control device 3 includes an energy output source 15, a processor 16, and a storage medium 17. The electric wirings 37 and 38 are arranged to extend through the inside the cable 13, and the other end of the respective electric wirings 37 and 38 is connected to the energy output source 15. The energy output source 15 includes a converter circuit that converts electric power obtained from a battery power source or a receptacle outlet fixed to a wall into electric energy supplied to the drive unit 30 of the ultrasound transducer 20, and outputs the converted electric energy. The electric energy output from the energy output source 15 is supplied to the drive unit 30 through the electric wirings 37 and 38. The energy output source 15 outputs alternating current power as electric energy to the drive unit 30.

The processor 16 serving as a control unit is constituted of an integrated circuit that includes a central processing unit (CPU), an application specific integrated circuit (ASIC), a field programmable gate array (FPGA), or the like. Processing in the processor 16 is performed according to a program stored in the processor 16 or the storage medium 17. Moreover, the storage medium 17 stores a processing program that is used by the processor 16, parameters, tables, and the like used for arithmetic operation by the processor 16. The processor 16 controls output of the electric energy from the energy output source 15 to the drive unit 30. The processor 16 adjusts a frequency in output of the electric energy from the energy output source 15 to a predetermined frequency.

When the electric energy is supplied from the energy output source 15 to the drive unit 30, a voltage is applied between the electrode members 32 and 33, and the voltage is applied to the respective piezoelectric devices 31. Thus, each of the respective piezoelectric devices 31 converts the electric energy into vibrational energy, and ultrasonic vibrations are generated by the piezoelectric device 31. The generated ultrasonic vibrations are propagated to the rod member 10, and are propagated in the rod member 10 from the proximal end side toward the distal end side, to the rod protruding portion 11. The end effector 7 treats a subject of treatment, such as a living tissue, by using the ultrasonic vibrations propagated to the rod protruding portion 11. In a state in which ultrasonic vibrations are being propagated to the ultrasound transducer 20 and the rod member 10, the vibrator including the ultrasound transducer 20 and the rod member 10 vibrates at a predetermined resonance frequency Frref. Therefore, in the ultrasound transducer 20, the distal end block 22, the proximal end block 23, and the drive unit 30 vibrate together by ultrasonic vibrations generated by the piezoelectric device 31. At this time, the vibrator makes vertical vibrations substantially parallel to the longitudinal axis L. An influence of fluctuations during operation is detected by the energy control device 3, and the electric energy is adjusted.

In a state in which the vibrator vibrates at the predetermined resonance frequency Frref, an antinode of ultrasonic vibration is generated at the distal end of the vibrator, that is the distal end of the rod member 10. Furthermore, an antinode of ultrasonic vibration is generated at the proximal end of the vibrator, that is, the proximal end of the ultrasound transducer 20.

Even the ultrasound transducer 20 alone vibrates at the predetermined resonance frequency Frref by ultrasonic vibrations generated by the piezoelectric device 31. The antinode of ultrasonic vibration is generated at the distal end of the distal end block 22 and the proximal end of the proximal end block 23. A node of ultrasonic vibration is generated at the supported portion 25 of the distal end block 22. At least one node of ultrasonic vibration is generated on the distal end side relative to the supported portion 25 in the distal end block 22.

The ultrasound transducer 20 described above is a minimum component unit of the ultrasound transducer 20, and is a derived unit of the bolt 21, the distal end block 22, the proximal end block 23, and the drive unit 30. The length of the ultrasound transducer 20 alone is a natural number multiple of a half wavelength of vertical vibration at the predetermined resonance frequency Frref. To the distal end side of the ultrasound transducer 20 alone, the rod member 10 is connected as a separate component.

In one implementation example, between the drive unit 30 and the distal end block 22, and between the drive unit 30 and the proximal end block 23, an insulator ring (not shown) made from an electrically insulating material is respectively provided. Furthermore, between an inner periphery of the drive unit 30 and an outer periphery of the bolt 21, an insulator tube (not shown) made from an electrically insulating material is provided. It is thus prevented the electric energy supplied to the drive unit 30 from being supplied to the distal end block 22, the proximal end block 23 and the bolt 21. Moreover, in one implementation example, electric energy different from the electric energy supplied to the drive unit 30 is output from the energy output source 15. For example, the electric energy different from the electric energy supplied to the drive unit 30 is respectively supplied to the rod protruding portion 11 and the jaw 12. Thus, a high-frequency electric current flows in the subject of treatment held between the jaw 12 and the rod protruding portion 11.

Next, a form of the distal end block 22 constituting the ultrasound transducer 20 is described.

Figure 2:
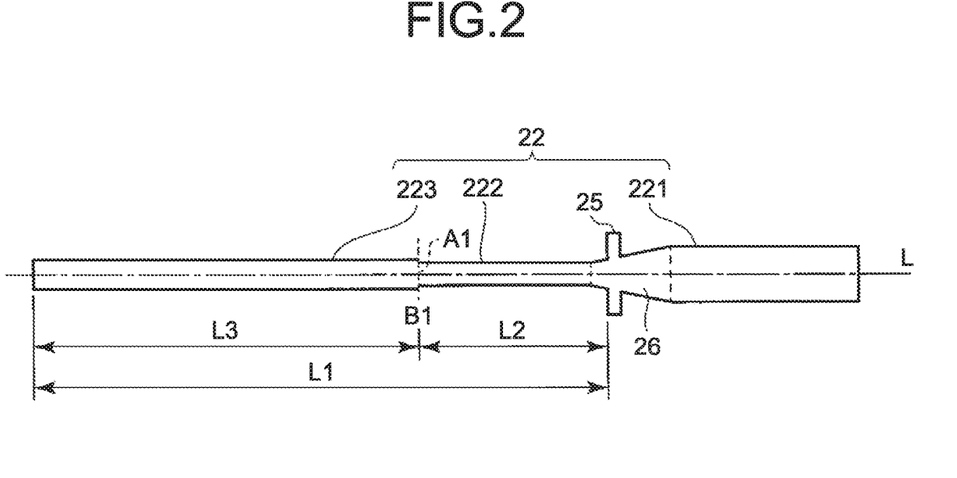
FIG. 2 is a cross-section of a distal end block constituting the ultrasound transducer according to an exemplary embodiment.

FIG. 2 is a cross-section of a distal end block constituting the ultrasound transducer 20 according to an exemplary embodiment. FIG. 2 depicts a cross section of the distal end block 22 substantially parallel to the longitudinal axis L. Assume that the distal end block 22 is made from a material having physical properties to be a reference.

The distal end block 22 includes a first portion 221, a second portion 222, and a third portion 223 sequentially arranged from the distal end side of the drive unit 30 along the longitudinal axis L. The first portion 221, the second portion 222, and the third portion 223 may be processed as a single element, or may be processed as respective separate elements.

The first portion 221 is adjacent to the piezoelectric device 31. In this first portion 221, for example, the supported portion 25 and the horn 26 described above are arranged.

The first portion 221 causes the piezoelectric device 31 to generate ultrasonic vibrations, and is configured such that a position of the supported portion 25 substantially corresponds to a node of the ultrasonic vibration in a state in which the ultrasonic vibrations are being propagated from the proximal end block 23 and the distal end block 22 (the first portion 221, the second portion 222, and the third portion 223). By such a configuration, the supported portion 25 is appropriately supported by the transducer case 18 or the housing 5.

The second portion 222 is arranged continuously to the distal end side of the first portion 221. The second portion 222 is in a cylindrical shape. A cross-sectional shape of the second portion 222 perpendicular to the longitudinal axis L is uniform or substantially uniform along the longitudinal axis L.

The third portion 223 is arranged continuously to the second portion 222. The third portion 223 is in a cylindrical shape. A cross-sectional shape of the third portion 223 perpendicular to the longitudinal axis L is substantially uniform along the longitudinal axis L. The third portion 223 is structured such that a cross-sectional area of a virtual plane perpendicular to the longitudinal axis L differs from that of the second portion 222.

The distal end of the third portion 223 causes the piezoelectric device 31 to generate ultrasonic vibrations as described above, and corresponds to or substantially corresponds to an antinode of the ultrasonic vibration in a state in which the ultrasonic vibrations are being propagated to the proximal end block 23 and the distal end block 22.

As used herein, "substantially corresponds to an antinode" or "substantially corresponds to a node" means that relevant portion of is formed on at least an outer periphery of the antinode or node. For example, the distal end of the third portion 223 substantially corresponds to an antinode of the ultrasonic vibration when it is formed on at least an outer periphery of the antinode.

Next, a position of a boundary between the second portion 222 and the third portion 223 (hereinafter, boundary A1) arranged in the distal end block 22 is described. The boundary A1 is on a virtual plane perpendicular to the longitudinal axis L.

The distal end block 22 causes the piezoelectric device 31 to generate ultrasonic vibrations, and is configured such that a position of the boundary A1 corresponds to or substantially corresponds to an antinode of ultrasonic vibration in a state in which the ultrasonic vibrations are being propagated to the proximal end block 23 and the distal end block 22. The purpose of this arrangement is to make it less likely for the distal end block 22 to have a transformation ratio of ultrasonic vibration near the boundary A1 between the second portion 222 and the third portion 223. Accordingly, an amplitude of ultrasonic vibration at the distal end of the ultrasound transducer 20 stays practically uniform, irrespective of the position of the boundary A1 under a condition that a distance between the supported portion 25 and the third portion 223 along the longitudinal axis L is a predetermined distance, and that a resonance frequency of vibration of the ultrasound transducer 20 is a predetermined resonance frequency.

Suppose that a distance from the supported portion 25 to the distal end of the third portion 223 along the longitudinal axis L is L1.

The boundary A1 is arranged at a position (hereafter, reference position B1) at which a distance from the supported portion 25 to the boundary A1 along the longitudinal axis L becomes a distance L2. The reference position B1 is a position at which the resonance frequency of vibration of the ultrasound transducer 20 becomes the predetermined resonance frequency Frref.

Suppose a distance from the boundary A1 to the distal end of the third portion 223 along the longitudinal axis L is L3. L3 corresponds to a distance from the reference position B1 that corresponds to or substantially corresponds to an antinode of ultrasonic vibration to the distal end of the third portion 223 that corresponds to or substantially corresponds to an antinode of ultrasonic vibration. Therefore, L3 is a natural number multiple of a half wavelength of ultrasonic vibration.

A relation of L1=L2+L3 holds.

Figure 3:
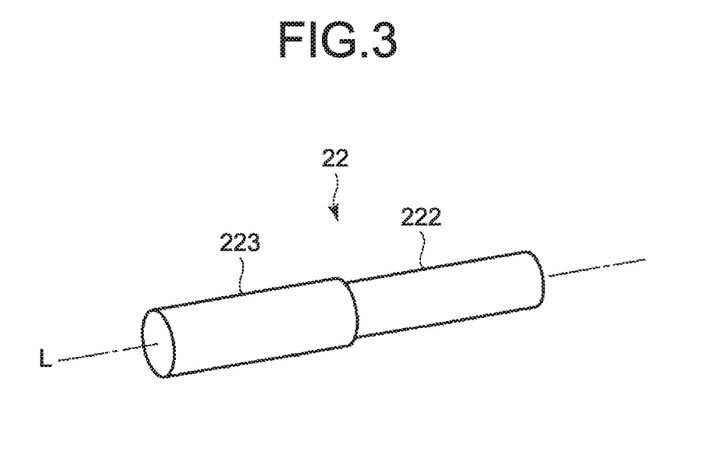
FIG. 3 is a perspective view of the distal end block constituting the ultrasound transducer according to an exemplary embodiment.

FIG. 3 is a perspective view of the distal end block 22 constituting the ultrasound transducer 20 as an example.

The second portion 222 and the third portion 223 have a cylindrical shape. A cross-sectional area of a virtual plane of the second portion 222 perpendicular to the longitudinal axis L is smaller than a cross-sectional area of a virtual plane of the third portion 223 perpendicular to the longitudinal axis L.

Figure 4:
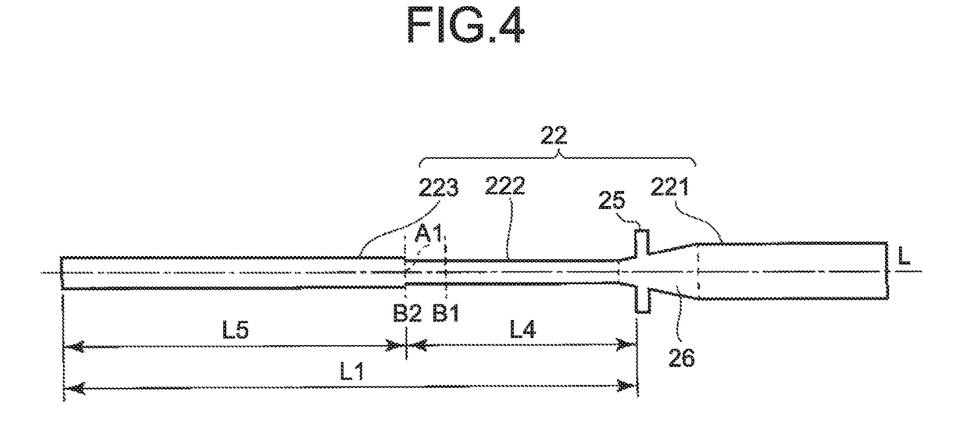
FIG. 4 is a cross section of the distal end block constituting the ultrasound transducer according to an exemplary embodiment.

Next, a configuration of the ultrasound transducer 20 in which a position of the boundary A1 is arranged at a position different from the reference position B1 under a condition that the distance L1 is constant is described.

FIG. 4 is a cross section of the distal end block 22 constituting the ultrasound transducer 20 as an example. FIG. 4 depicts a cross section of the distal end block 22 substantially parallel to the longitudinal axis L. FIG. 4 illustrates the ultrasound transducer 20 in which a position of the boundary A1 is distal of the reference position B1. The distal end block 22 illustrated in FIG. 4 is made from a material having physical properties to be a reference, similarly to the distal end block 22 illustrated in FIG. 2.

A position of the arbitrary boundary A1 on a distal side of the reference position B1 is a position B2.

A distance from the supported portion 25 to the position B2 along the longitudinal axis L is L4.

A distance from the position B2 to the distal end of the third portion 223 along the longitudinal axis L is L5.

A relation of L1=L4+L5 holds.

L4 is longer than L2 in FIG. 2. L5 is shorter than L3 in FIG. 2.

The resonance frequency of vibration of the ultrasound transducer 20 is higher when the boundary A1 is positioned at the position B2 on the distal side of the reference position B1 than when the boundary A1 is positioned at the reference position B1. Characteristics of the resonance frequency of vibration of the ultrasound transducer 20 according to the position of the boundary A1 are described later.

Figure 5:
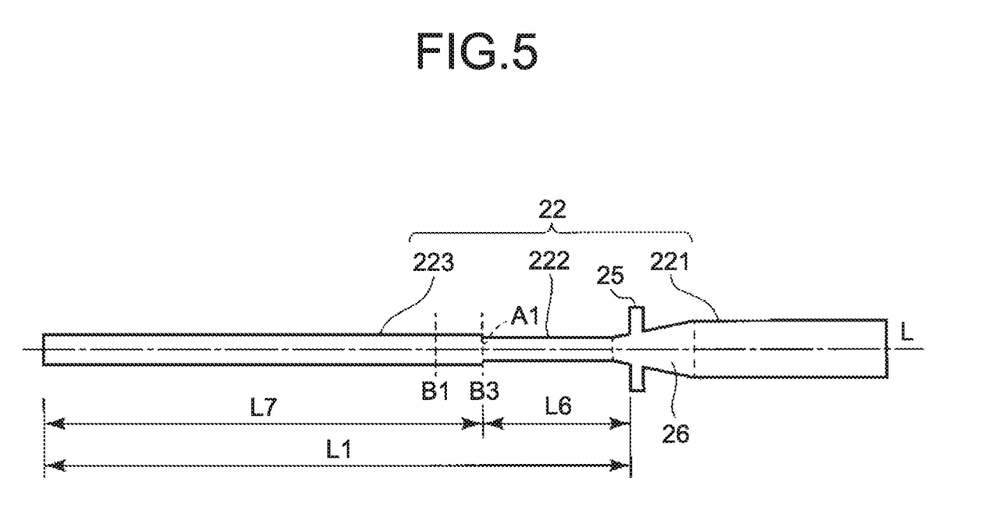
FIG. 5 is a cross section of the distal end block constituting the ultrasound transducer according to an exemplary embodiment.

FIG. 5 is a cross section of the distal end block 22 constituting the ultrasound transducer 20 as an example. FIG. 5 depicts a cross section of the distal end block 22 substantially parallel to the longitudinal axis L. FIG. 5 illustrates the ultrasound transducer 20 in which the boundary A1 is positioned on a proximal side (the supported portion 25) side of the reference position B1. The distal end block 22 illustrated in FIG. 5 is made from a material having physical properties to be a reference similarly to the distal end block 22 illustrated in FIG. 2.

A position of the arbitrary boundary A1 on the proximal (supported portion 25) side of the reference position B1 is B3.

A distance from the supported portion 25 to the position B3 along the longitudinal axis L is L6.

A distance from the position B3 to the distal end of the third portion 223 along the longitudinal axis L is L7.

A relation of L1=L6+L7 holds.

L6 is shorter than L2 in FIG. 2. L7 is longer than L3 in FIG. 2.

The resonance frequency of vibration of the ultrasound transducer 20 is lower when the boundary A1 is positioned at the position B3 on the proximal (supported portion 25) side of the reference position B1 than when the boundary A1 is positioned at the reference position B1. Characteristics of the resonance frequency of vibration of the ultrasound transducer 20 according to the position of the boundary A1 are described below.

Figure 6:
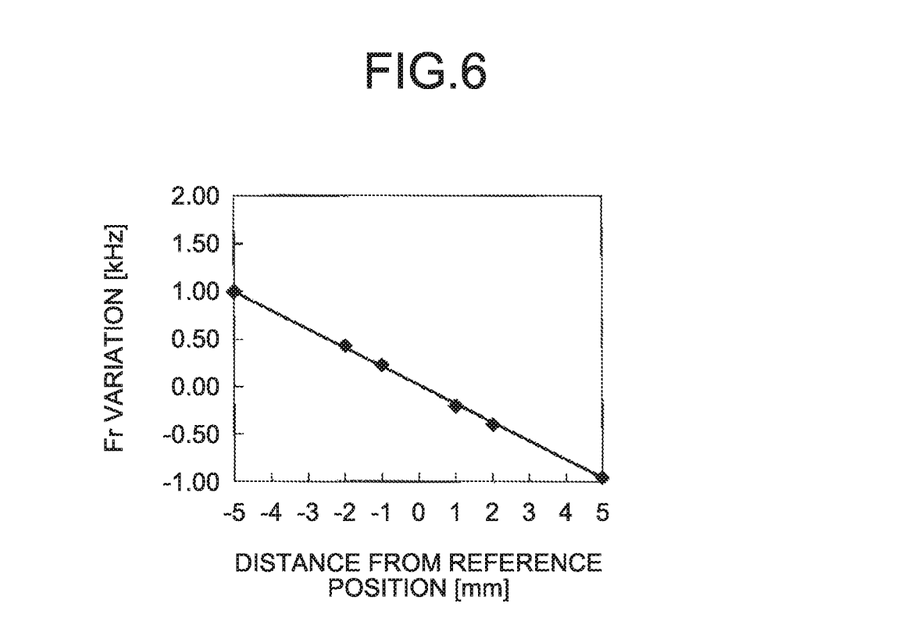
FIG. 6 is a graph of characteristics of resonance frequency of vibrations by the ultrasound transducer according to an exemplary embodiment.

FIG. 6 is a graph of characteristics of resonance frequency of vibrations by the ultrasound transducer 20 according to the position of the boundary A1.

A horizontal axis represents a distance from the reference position B1 to the boundary A1 in the longitudinal axis L. A negative direction of a horizontal axis is a direction from the reference position B1 toward the distal side of the distal end block 22. A positive direction of the horizontal axis is a direction from the reference position B1 toward the proximal (supported portion 25) side.

When a value of the horizontal axis is 0, the boundary A1 is at the reference position B1. That is, the distal end block 22 is configured as illustrated in FIG. 2. When a value of the horizontal axis is a negative value, the boundary A1 is positioned at the position B2. That is, the distal end block 22 is configured as illustrated in FIG. 4. When a value of the horizontal axis is a positive value, the boundary A1 is positioned at the position B3. That is, the distal end block 22 is configured as illustrated in FIG. 5.

A vertical axis represents a variation in the resonance frequency of vibration of the ultrasound transducer 20. The variation corresponds to a difference between the resonance frequency of vibration of the ultrasound transducer 20 and the predetermined resonance frequency Frref.

When the boundary A1 is at the reference position B1, the resonance frequency of vibration of the ultrasound transducer 20 is the predetermined resonance frequency Frref. When the boundary A1 is positioned at the position B2, a difference between the resonance frequency of vibration of the ultrasound transducer 20 and the predetermined resonance frequency Frref takes a positive value. That is, when the boundary A1 is at the position B2, the resonance frequency of vibration of the ultrasound transducer 20 is higher than the predetermined resonance frequency Frref. When the boundary A1 is at the position B3, a difference between the resonance frequency of vibration of the ultrasound transducer 20 and the predetermined resonance frequency Frref takes a negative value. That is, when the boundary A1 is at the position B3, the resonance frequency of vibration of the ultrasound transducer 20 is lower than the predetermined resonance frequency Frref.

As described, under a condition that the distance L1 is constant, the resonance frequency of vibration of the ultrasound transducer 20 varies according to the position of the boundary A1. Specifically, as the position of the boundary A1 comes closer to the supported portion 25 from the distal end side of the third portion 223, the resonance frequency of vibration of the ultrasound transducer 20 linearly or substantially linearly decreases.

Next, the distal end block 22 constituting the ultrasound transducer 20 according to other exemplary embodiments are described, with reference to FIG. 7 to FIG. 10. In the following description, a form of the distal end block 22 is only an example. The form of the distal end block 22 is not limited to the form described in the present application as long as it is configured such that a cross-sectional area of the second portion 222 of a virtual plane perpendicular to the longitudinal axis L is smaller than a cross-sectional area of the third portion 223.

Figure 7:
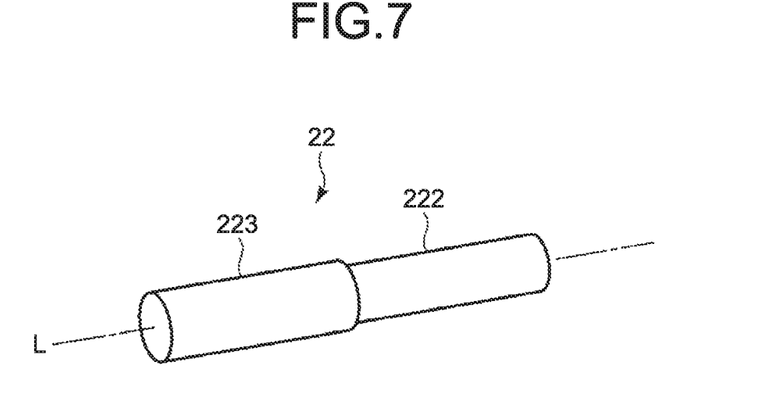
FIG. 7 is a perspective view of the distal end block constituting the ultrasound transducer according to an exemplary embodiment.

FIG. 7 is a perspective view of the distal end block 22 constituting the ultrasound transducer 20 according to an exemplary embodiment. The second portion 222 and the third portion 223 are formed in an ecliptic cylindrical shape.

Figure 8:
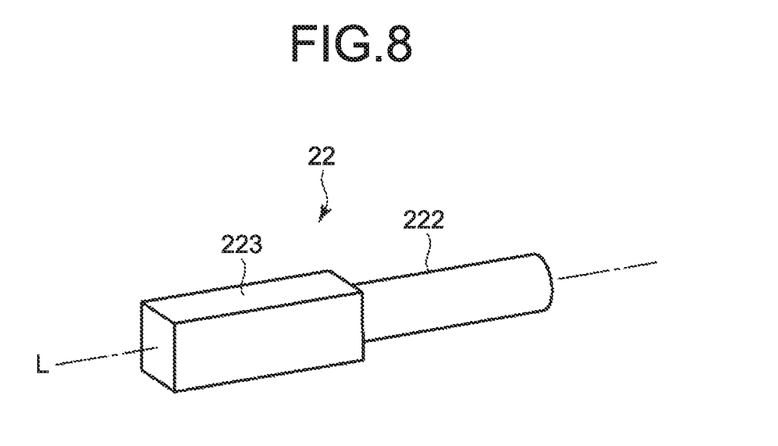
FIG. 8 is a perspective view of the distal end block constituting the ultrasound transducer according to an exemplary embodiment.

FIG. 8 is a perspective view of the distal end block 22 constituting the ultrasound transducer 20 according to another exemplary embodiment. The second portion 222 is structured in a cylinder. The third portion 223 is structured in a quadrangular prism. As described, a shape of a cross section of the second portion 222 on a virtual plane is not necessarily required to be a similar figure to a cross section of the third portion 223 on a virtual plane perpendicular to the longitudinal axis L. The third portion 223 may be configured in a polygonal prism other than a quadrangular prism.

Figure 9:
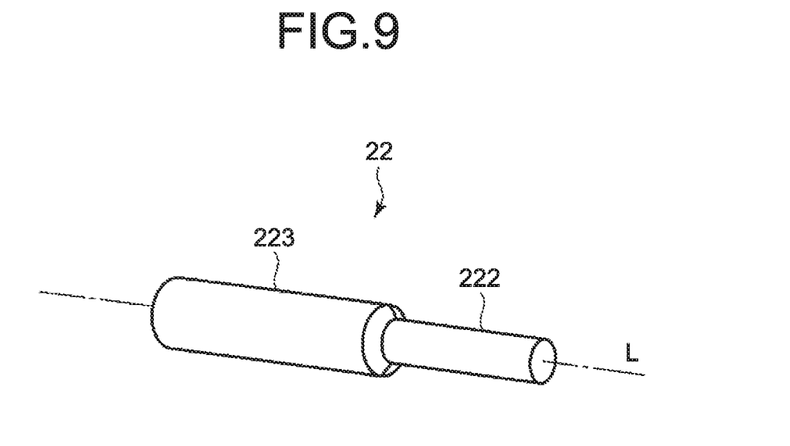
FIG. 9 is a perspective view of the distal end block constituting the ultrasound transducer according to an exemplary embodiment.

FIG. 9 is a perspective view of the distal end block 22 constituting the ultrasound transducer according to another exemplary embodiment. In a portion near the boundary A1, the second portion 222 is structured in a gently changing shape in which outer dimensions (cross-sectional area) gradually decrease as it approaches the supported portion 25 away from the boundary A1. Instead of this arrangement, it may be arranged such that the third portion 223 is structured in a gently changing shape (tapered shape) in which outer dimensions (cross-sectional area) of the third portion 223 gradually decrease as it approaches the boundary A1 away from the distal end side of the third portion 223 in a portion near the boundary A1. The gently changing shape near the boundary A1 suppresses the concentration of stress on the boundary A1 when ultrasonic vibrations are propagated by the ultrasound transducer 20, compared with a case in which the boundary A1 is structured in a stepped shape. Therefore, the distal end block 22 is less likely to be damaged.

Figure 10:
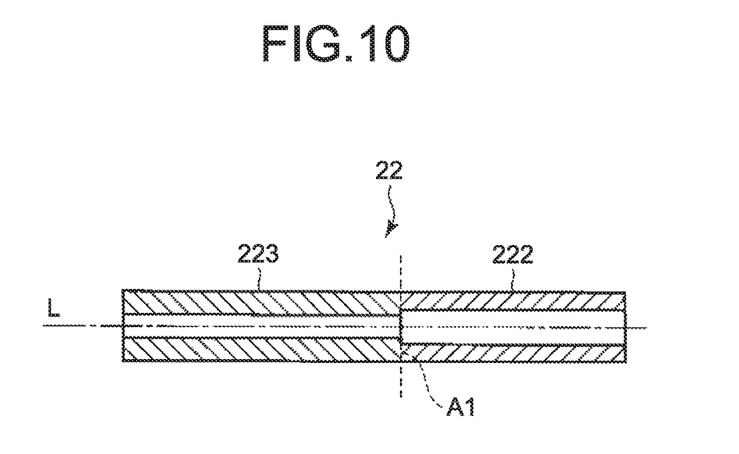
FIG. 10 is a cross section of the distal end block constituting the ultrasound transducer according to an exemplary embodiment.

FIG. 10 is a cross section of the distal end block constituting the ultrasound transducer according to another exemplary embodiment. FIG. 10 depicts a cross section of the distal end block 22 substantially parallel to the longitudinal axis L. The second portion 222 and the third portion 223 are in a tubular shape. A form of an outer periphery of the second portion 222 is the same as a form of an outer periphery of the third portion 223 on virtual planes perpendicular to the longitudinal axis L. Therefore, a change in outer dimensions of the distal end block 22 around the boundary A1 is eliminated. A length of an inner periphery of the second portion 222 on a virtual plane perpendicular to the longitudinal axis L is shorter than a length of an inner periphery of the third portion 223. Therefore, a cross-sectional area of the second portion 222 on a virtual plane perpendicular to the longitudinal axis L is smaller than a cross-sectional area of the third portion 223.

Forms of the outer periphery and the inner periphery of the second portion 222 on a virtual plane perpendicular to the longitudinal axis L may be a circular shape or a polygonal shape. The form of the outer periphery of the second portion 222 may be a similar figure to the form of the inner periphery of the second portion 222, or may be non-similar figure. Forms of the outer periphery and the inner periphery of the third portion 223 on virtual planes perpendicular to the longitudinal axis L may be a circular shape or a polygonal shape. The form of the outer periphery of the third portion 223 may be a similar figure to the form of the inner periphery of the third portion 223 or may be non-similar figure.

Note that it is preferable that the distal end block 22 be structured to have a cross-sectional shape on a virtual plane perpendicular to the longitudinal axis L having as many symmetry axes as possible. A preferable example is a circular shape illustrated in FIG. 3. This is because with more symmetry axes, it is possible to reduce a possibility that the distal end block 22 shows an unpreferable action such as vibrating in a direction other than the direction along the longitudinal axis L.

In some of the examples described above, a cross-sectional shape of the second portion 222 perpendicular to the longitudinal axis L is uniform or substantially uniform along the longitudinal axis L, but it is not limited thereto. The entire second portion 222 may have a tapered shape along the longitudinal axis L, or may have variations in cross-sectional area in a stepped manner. Similarly, the entire third portion 223 may have a tapered shape along the longitudinal axis L, or may have variations in cross-sectional area in a stepped manner.

Next, adjustment of the position of the boundary A1 is described.

As an example, adjustment of the position of the boundary A1 is performed at a designing stage of the ultrasound transducer 20, or at the time of setting process dimensions. The position of the boundary A1 may be calculated based on a difference between physical properties of a material forming the distal end block 22 and physical properties to be a reference. The ultrasound transducer 20 is processed such that the boundary A1 is arranged at a position adjusted from the reference position B1.

A case in which the distal end block 22 is made from a material having physical properties to be a reference is assumed. In this case, the ultrasound transducer 20 is processed such that the boundary A1 is arranged at the reference position B1. Thus, the ultrasound transducer 20 vibrates at one resonance frequency. The resonance frequency at this time is assumed to be the desired predetermined resonance frequency Frref.

Next, a case in which the distal end block 22 is made from a material having different physical properties from the physical properties to be a reference. In one case, when the boundary A1 is arranged at the reference position B1, the resonance frequency of vibration of the ultrasound transducer 20 can be lower than the predetermined resonance frequency Frref. By processing such that the boundary A1 is arranged at the position B2 for which a distance from the reference position B1 is appropriately adjusted, the ultrasound transducer 20 vibrates at the predetermined resonance frequency Frref. In another case, when the boundary A1 is arranged at the reference position B1, the resonance frequency of vibration of the ultrasound transducer 20 can be higher than the predetermined resonance frequency Frref. By processing such that the boundary A1 is arranged at the position B3 for which a distance from the reference position B1 is appropriately adjusted, the ultrasound transducer 20 vibrates at the predetermined resonance frequency Frref.

In still another example, adjustment of the position of the boundary A1 may be performed for the distal end block 22 being a state of part, or an actual item (ultrasound transducer 20) in a state of being assembled. In this case, the distal end block 22 is shaved to adjust the position of the boundary A1 such that the resonance frequency of vibration of the ultrasound transducer 20 becomes the predetermined resonance frequency Frref. The adjustment of the position of the boundary A1 in this example is adjustment toward a direction to bring the position of the boundary A1 closer to the distal end side of the third portion 223. That is, when the resonance frequency of vibration of the ultrasound transducer 20 is lower than the predetermined resonance frequency Frref, the position of the boundary A1 is adjusted such that the resonance frequency of vibration of the ultrasound transducer 20 rises to the predetermined resonance frequency Frref.

Next, an effect of the above exemplary embodiments show, for example, in FIGS. 2-10 is described.

The ultrasound transducer 20 is configured to vibrate at the predetermined resonance frequency Frref under a condition that a distance from the supported portion 25 to the distal end of the third portion 223 is a predetermined distance. The ultrasound transducer 20 is configured such that a length L1 from the supported portion 25 of the distal end block 22 to the distal end of the third portion 223 along the longitudinal axis L is always constant even if the physical properties of a material forming the distal end block 22 of the ultrasound transducer 20 vary. Therefore, a need for changing sizes of other components is not generated when installing the ultrasound transducer 20 in the other components constituting the ultrasound treatment tool 2.

The ultrasound transducer 20 according to another exemplary embodiment is described.

This embodiment differs from the above embodiments shown in, for example, FIGS. 2-5 and 7-10 in a form of the distal end block 22 constituting the ultrasound transducer 20. In this embodiment, configurations different from the above exemplary embodiments are described. As for a configuration of the present embodiment that may be the same as the above embodiments, explanation thereof is omitted.

Figure 11:
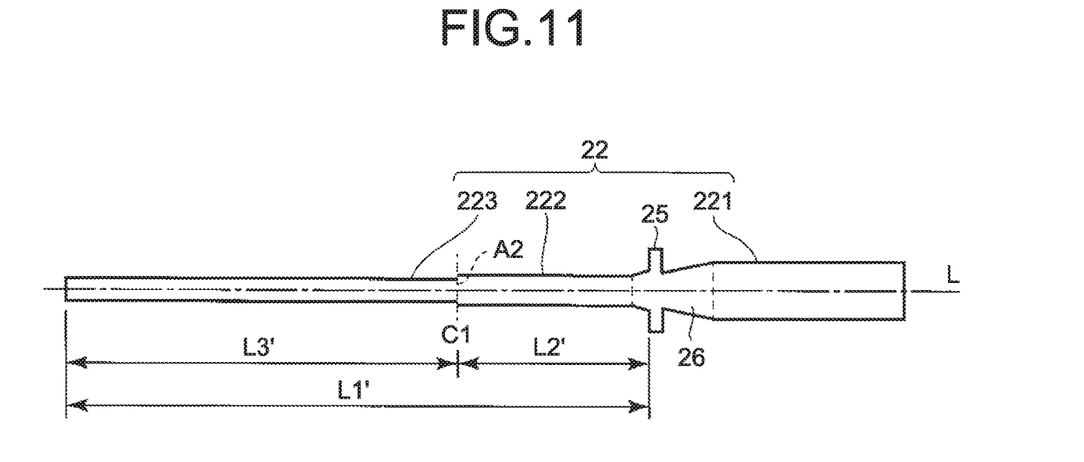
FIG. 11 is a cross section of a distal end block constituting the ultrasound transducer according to an exemplary embodiment.

FIG. 11 is a cross section of a distal end block 22 constituting the ultrasound transducer 20 as an example. FIG. 11 depicts a cross section of the distal end block 22 substantially parallel to the longitudinal axis L. Assume that the distal end block 22 is made from a material having physical properties to be a reference.

The distal end block 22 includes the first portion 221, the second portion 222, and the third portion 223, sequentially from the distal end side of the drive unit 30 along the longitudinal axis L. The first portion 221, the second portion 222, and the third portion 223 may be processed as a single element, or may be processed as respective separate elements.

In the first portion 221, the supported portion 25 and the horn 26 described above are formed.

The first portion 221 causes the piezoelectric device 31 to generate ultrasonic vibrations, and is configured such that a position of the supported portion 25 substantially corresponds to or substantially corresponds to a node of the ultrasonic vibration in a state in which the ultrasonic vibrations are being propagated to the proximal end block 23 and the distal end block 22. The purpose of this is the same as the purpose described with respect to the above exemplary embodiments illustrated in, for example, FIGS. 2-5 and 7-10.

The second portion 222 is arranged continuously to the distal end side of the first portion 221. The second portion 222 is in a cylindrical shape. A cross-sectional shape of the second portion 222 perpendicular to the longitudinal axis L is uniform or substantially uniform along the longitudinal axis L.

The third portion 223 is arranged continuously to the second portion 222. The third portion 223 is in a cylindrical shape. A cross-sectional shape of the third portion 223 perpendicular to the longitudinal axis L is uniform or substantially uniform along the longitudinal axis L. The third portion 223 is structured such that a cross-sectional area of a virtual plane perpendicular to the longitudinal axis L differs from that of the second portion 222.

The distal end of the third portion 223 causes the piezoelectric device 31 to generate ultrasonic vibrations, and corresponds to or substantially corresponds to an antinode of ultrasonic vibration in a state in which the ultrasonic vibrations are being propagated to the proximal end block 23 and the distal end block 22.

Next, a position of a boundary (hereinafter, boundary A2) between the second portion 222 and the third portion 223 arranged in the distal end block 22 is described. The boundary A2 is positioned on a virtual plane perpendicular to the longitudinal axis L.

The distal end block 22 causes the piezoelectric device 31 to generate ultrasonic vibrations, and is configured such that the position of the boundary A2 corresponds to or substantially corresponds to an antinode of ultrasonic vibration in a state in which the ultrasonic vibrations are being propagated to the proximal end block 23 and the distal end block 22. The purpose of this is same as the purpose described with respect to the above exemplary embodiments illustrated in, for example, FIGS. 2-5 and 7-10.

A distance from the supported portion 25 to the distal end of the third portion 223 along the longitudinal axis L is L1'.

The boundary A2 is arranged at a position (hereinafter, reference position C1) at which the distance from the supported portion 25 to the boundary A2 along the longitudinal axis L is L2'. The reference position C1 is a position at which the resonance frequency of vibration of the ultrasound transducer 20 becomes the predetermined resonance frequency Frref.

A distance from the boundary A2 to the distal end of the third portion 223 along the longitudinal axis L is L3'. L3' corresponds to a distance from the reference position C1 that corresponds to or substantially corresponds to an antinode of ultrasonic vibration to the distal end of the third portion 223 that corresponds to or substantially corresponds to an antinode of ultrasonic vibration. Therefore, L3' is natural number multiple of a half wavelength of ultrasonic vibration.

A relation of L1'=L2'+L3' holds.

Figure 12:
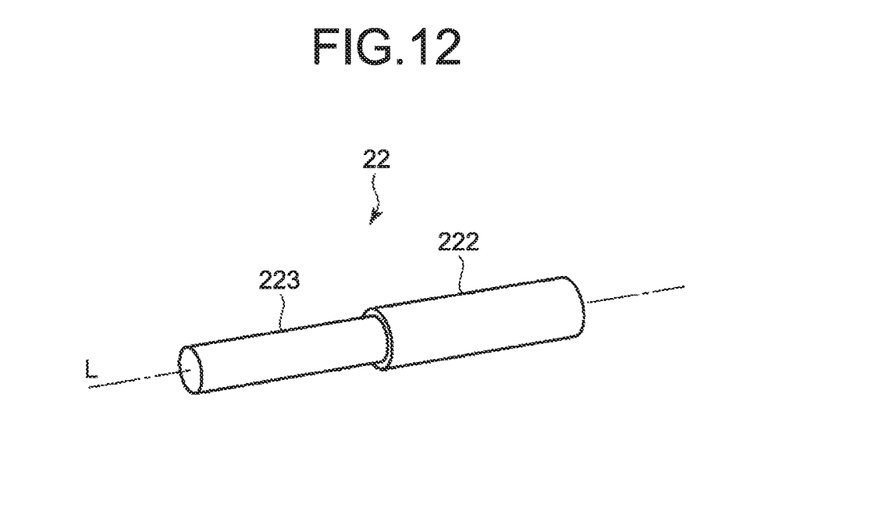
FIG. 12 is a perspective view of the distal end block constituting the ultrasound transducer according to an exemplary embodiment.

FIG. 12 is a perspective view of the distal end block 22 constituting the ultrasound transducer 20 as an example.

The second portion 222 and the third portion 223 have a cylindrical shape. A cross-sectional area of a virtual plane of the second portion 222 perpendicular to the longitudinal axis L is larger than a cross-sectional area of a virtual plane of the third portion 223 perpendicular to the longitudinal axis L.

The distal end block 22 may be structured such that outer dimensions gently change near the boundary A2. The reason is the same as the reason described with respect to the above exemplary embodiments illustrated in, for example, FIGS. 2-5 and 7-10.

Figure 13:
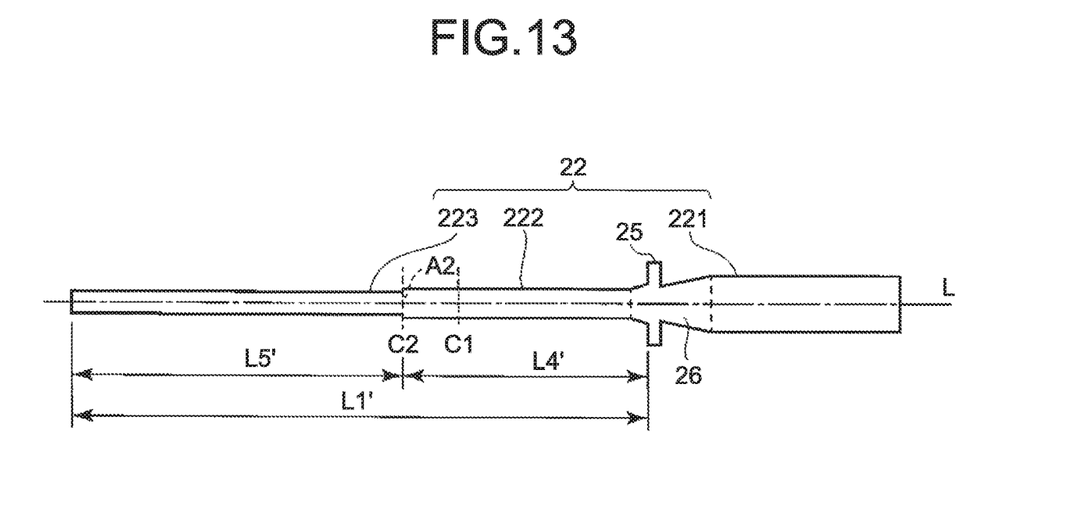
FIG. 13 is a cross section of the distal end block constituting the ultrasound transducer according to an exemplary embodiment.

Next, a configuration of the ultrasound transducer 20 in which a position of the boundary A2 is arranged at a position different from the reference position C1 under a condition that the distance L1' is constant is described.

FIG. 13 is a cross section of the distal end block 22 constituting the ultrasound transducer 20 as an example. FIG. 13 depicts a cross section of the distal end block 22 substantially parallel to the longitudinal axis L. FIG. 13 illustrates the ultrasound transducer 20 in which the boundary A2 is positioned distal of the reference position C1. The distal end block 22 illustrated in FIG. 13 is made from a material having physical properties to be a reference similarly to the distal end block 22 illustrated in FIG. 11.

A position of the boundary A1 on the distal side of the reference position C1 is a position C2.

A distance from the supported portion 25 to the position C2 along the longitudinal axis L is L4'.

A distance from the position C2 to the distal end of the third portion 223 along the longitudinal axis L is L5'.

A relation of L1'=L4'+L5' holds.

L4' is longer than L2' in FIG. 2. L5' is shorter than L3' in FIG. 2.

The resonance frequency of vibration of the ultrasound transducer 20 is lower when the boundary A2 is positioned at the position C2 on the distal side of the reference position C1 than when the boundary A2 is positioned at the reference position C1. Characteristics of the resonance frequency of vibration of the ultrasound transducer 20 according to the position of the boundary A2 are described later.

Figure 14:
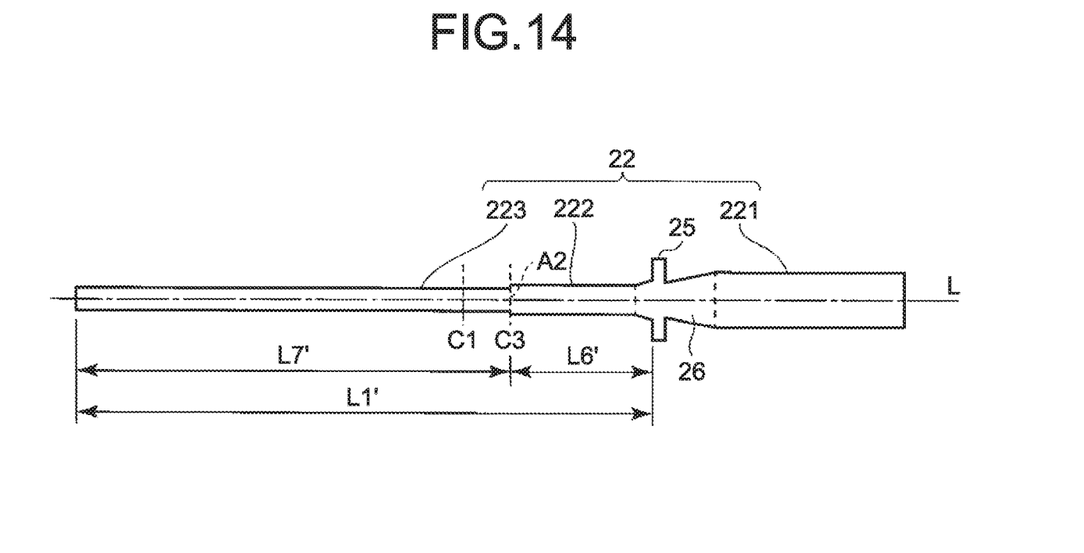
FIG. 14 is a cross-section of the distal end block constituting the ultrasound transducer according to an exemplary embodiment.

FIG. 14 is a cross section of the distal end block 22 constituting the ultrasound transducer 20 as an example. FIG. 14 depicts a cross section of the distal end block 22 substantially parallel to the longitudinal axis L. FIG. 14 illustrates the ultrasound transducer 20 in which the boundary A2 is positioned on the proximal (supported portion 25) side of the reference position C1 under a condition that the distance L1' is constant. The distal end block 22 illustrated in FIG. 14 is made from a material having physical properties to be a reference similarly to the distal end block 22 illustrated in FIG. 11.

A position of the arbitrary boundary A2 on the proximal (supported portion 25) side of the reference position C1 is C3.

A distance from the supported portion 25 to the position C3 along the longitudinal axis L is L6'.

A distance from the position C3 to the distal end of the third portion 223 along the longitudinal axis L is L7'.

A relation of L1'=L6'+L7' holds.

L6' is shorter than L2 in FIG. 2. L7' is longer than L3 in FIG. 2.

The resonance frequency of vibration of the ultrasound transducer 20 is higher when the boundary A2 is positioned at the position C3 on the proximal (supported portion 25) side of the reference position C1 than when the boundary A1 is positioned at the reference position C1.

Characteristics of the resonance frequency of vibration of the ultrasound transducer 20 according to the position of the boundary A2 are described.

When the boundary A2 is positioned at the reference position C1, the resonance frequency of vibration of the ultrasound transducer 20 is the predetermined resonance frequency Frref. When the boundary A2 is positioned at the position C2, the resonance frequency of vibration of the ultrasound transducer 20 is lower than the predetermined resonance frequency Frref. When the boundary A2 is positioned at the position C3, the resonance frequency of vibration of the ultrasound transducer 20 is higher than the predetermined resonance frequency Frref.

That is, under a condition that the distance L1' is constant, the resonance frequency of vibration of the ultrasound transducer 20 varies according to the position of the boundary A2. Specifically, as the position of the boundary A2 comes closer to the supported portion 25 from the distal end side of the third portion 223, the resonance frequency of vibration of the ultrasound transducer 20 linearly or substantially linearly increases.

As described, characteristics of the resonance frequency in this embodiment are inverse to the characteristics of the resonance frequency in the above exemplary embodiments, shown in, for example, FIGS. 2-5 and 7-10. The reason is because a magnitude relationship of a cross-sectional area of the second portion 222 and a cross-sectional area of the third portion 223 on a virtual plane perpendicular to the longitudinal axis L of the present embodiment is inverse to that of the above embodiments shown in FIGS. 2-5 and 7-10.

Figure 15:
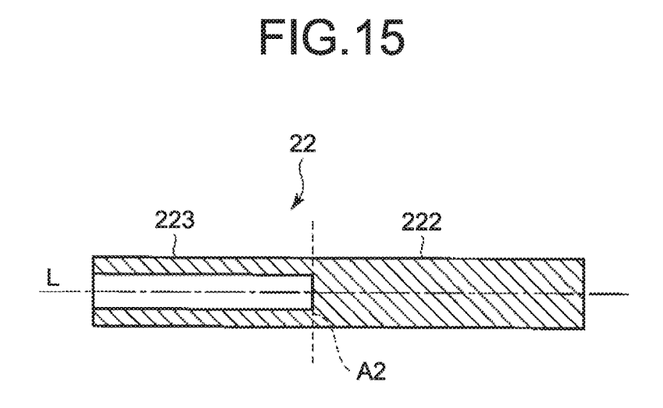
FIG. 15 is a cross section of the distal end block constituting the ultrasound transducer according to an exemplary embodiment.
Figure 16:
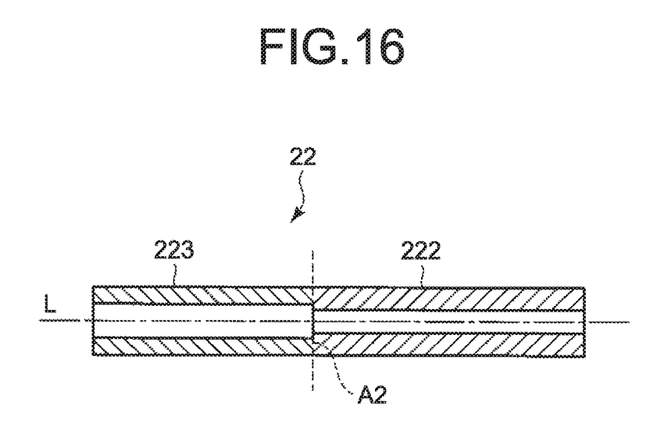
FIG. 16 is a cross section of the distal end block constituting the ultrasound transducer according to an exemplary embodiment.
Figure 17:
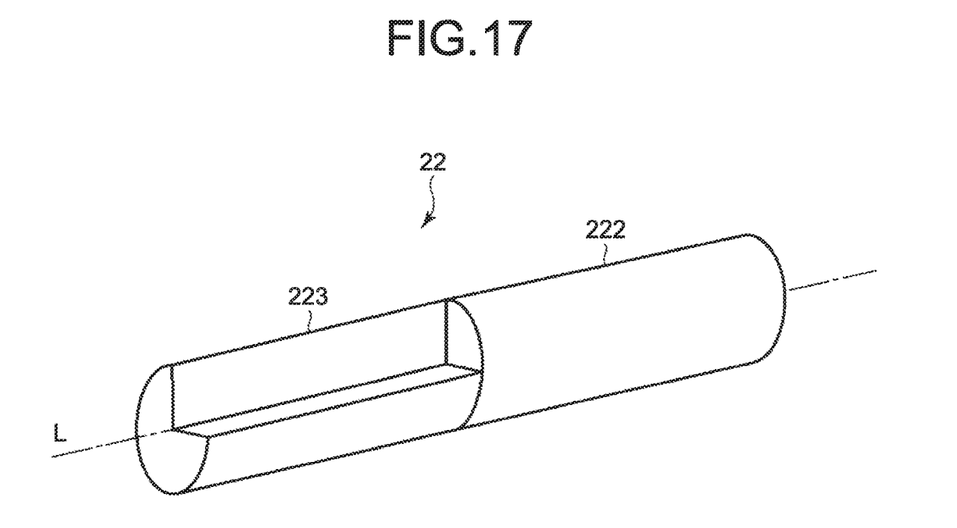
FIG. 17 is a perspective view of the distal end block constituting the ultrasound transducer according to an exemplary embodiment.

Next, alternative embodiments of the distal end block 22 constituting the ultrasound transducer 20 are described, with reference to FIG. 15 to FIG. 17. In the following description, a form of the distal end block 22 is only an example. The form of the distal end block 22 is not limited to the form described in the present application as long as it is configured such that a cross-sectional area of the second portion 222 of a virtual plane perpendicular to the longitudinal axis L is larger than a cross-sectional area of the third portion 223.

FIG. 15 is a perspective view of the distal end block 22 constituting the ultrasound transducer 20 of an exemplary embodiment. FIG. 15 depicts a cross section of the distal end block 22 substantially parallel to the longitudinal axis L. A form of an outer periphery of the second portion 222 is the same as a form of an outer periphery of the third portion 223 on a virtual plane perpendicular to the longitudinal axis L. The second portion 222 is in a pillar shape. The third portion 223 is formed in a tubular shape. Therefore, a cross-sectional area of the second portion 222 is larger than a cross-sectional area of the third portion 223 on virtual planes perpendicular to the longitudinal axis L. A form of the outer periphery of the second portion 222 on a virtual plane perpendicular to the longitudinal axis L may be a circular shape or a polygonal shape. Forms of the outer periphery and the inner periphery of the third portion 223 on a virtual plane perpendicular to the longitudinal axis L may be a circular shape or a polygonal shape. The form of the outer periphery of the third portion 223 may be a similar figure to the form of the inner periphery of the third portion 223 or may be non-similar figure.

FIG. 16 is a perspective view of the distal end block 22 constituting the ultrasound transducer 20 of an exemplary embodiment. FIG. 16 depicts a cross section of the distal end block 22 substantially parallel to the longitudinal axis L. A form of an outer periphery of the second portion 222 on a virtual plane perpendicular to the longitudinal axis L is the same as a form of an outer periphery of the third portion 223. The second portion 222 and the third portion 223 are in a pillar shape. However, the form of the outer periphery of the second portion 222 is smaller than the form of the outer periphery of the third portion 223 on virtual planes perpendicular to the longitudinal axis L. Therefore, a cross-sectional area of the second portion 222 is larger than a cross-sectional area of the third portion 223 on the virtual planes perpendicular to the longitudinal axis L.

A form of the outer periphery of the second portion 222 on a virtual plane perpendicular to the longitudinal axis L may be a circular shape or a polygonal shape. Forms of the outer periphery and the inner periphery of the third portion 223 on a virtual plane perpendicular to the longitudinal axis L may be a circular shape or a polygonal shape. The form of the outer periphery of the second portion 222 may be a similar figure to the form of the inner periphery of the second portion 222, or may be a non-similar figure. Forms of the outer periphery and the inner periphery of the third portion 223 on a virtual plane perpendicular to the longitudinal axis L may be a circular shape or a polygonal shape. The form of the outer periphery of the third portion 223 may be a similar figure to the form of the inner periphery of the third portion 223 or may be a non-similar figure.

FIG. 17 is a perspective view of the distal end block 22 constituting the ultrasound transducer 20 of an exemplary embodiment.

The second portion 222 is in a pillar shape. The third portion 223 is structured such that a form of the outer periphery of the third portion 223 on a virtual plane perpendicular to the longitudinal axis L is a shape of the outer periphery of the second portion 222 from which part thereof is notched. Therefore, a cross-sectional area of the second portion 222 is larger than a cross-sectional area of the third portion 223.

Note that it is preferable that the distal end block 22 be structured to have a cross-sectional shape on a virtual plane perpendicular to the longitudinal axis L having as many symmetry axes as possible. A preferable example is a circular shape illustrated in FIG. 12. The reason is the same as the reason described with respect to the above exemplary embodiments.

In some of the examples described above, a cross-sectional shape of the second portion 222 perpendicular to the longitudinal axis L is uniform or substantially uniform along the longitudinal axis L, but it is not limited thereto. The entire second portion 222 may have a tapered shape along the longitudinal axis L. Similarly, the entire third portion 223 may have a tapered shape along the longitudinal axis L.

Next, adjustment of the position of the boundary A2 is described.

As an example, adjustment of the position of the boundary A2 is performed at a designing stage of the ultrasound transducer 20, or at the time of setting process dimensions. The position of the boundary A2 may be calculated based on a difference between physical properties of a material forming the distal end block 22 and physical properties to be a reference. The ultrasound transducer 20 is processed such that the boundary A2 is arranged at a position adjusted from the reference position C1.

A case in which the distal end block 22 is made from a material having physical properties to be a reference is assumed. In this case, the ultrasound transducer 20 is processed such that the boundary A2 is arranged at the reference position C1. Thus, the ultrasound transducer 20 vibrates at one resonance frequency. The resonance frequency at this time is assumed to be the desired predetermined resonance frequency Frref.

Next, a case in which the distal end block 22 is made from a material having different physical properties from the physical properties to be a reference. In one case, when the boundary A2 is arranged at the reference position C1, the resonance frequency of vibration of the ultrasound transducer 20 can be lower than the predetermined resonance frequency Frref. By processing such that the boundary A2 is arranged at the position C3 for which a distance from the reference position C1 is appropriately adjusted, the ultrasound transducer 20 vibrates at the predetermined resonance frequency Frref. In another case, when the boundary A2 is arranged at the reference position C1, the resonance frequency of vibration of the ultrasound transducer 20 can be higher than the predetermined resonance frequency Frref. By processing such that the boundary A1 is arranged at the position C2 for which a distance from the reference position C1 is appropriately adjusted, the ultrasound transducer 20 vibrates at the predetermined resonance frequency Frref.

In still another example, adjustment of the position of the boundary A2 may be performed for the distal end block 22 being a state of part, or an actual item (ultrasound transducer 20) in a state of being assembled. In this case, the distal end block 22 is shaved to adjust the position of the boundary A2 such that the resonance frequency of vibration of the ultrasound transducer 20 becomes the predetermined resonance frequency Frref. The adjustment of the position of the boundary A2 in this example is adjustment toward a direction to bring the position of the boundary A2 closer to the supported portion 25. That is, when the resonance frequency of vibration of the ultrasound transducer 20 is lower than the predetermined resonance frequency Frref, the position of the boundary A2 is adjusted such that the resonance frequency of vibration of the ultrasound transducer 20 rises to the predetermined resonance frequency Frref.

The ultrasound transducer 20 according to the present embodiment enables to obtain an effect similar to that described with respect to the above embodiments.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising:
   an ultrasonic vibrator including a piezoelectric device configured to generate ultrasonic vibration from supplied electric energy along a longitudinal axis;
   a proximal end block arranged on a proximal end side of the ultrasonic vibrator along the longitudinal axis; and
   a distal end block arranged on a distal end side of the ultrasonic vibrator opposite to the proximal end side, the distal end block including, sequentially in a direction from a proximal end to a distal end of the distal end block along the longitudinal axis:
      a first portion adjacent to the piezoelectric device, the first portion including a supported portion;
      a second portion adjacent to the first portion; and
      a third portion adjacent to the second portion, the third portion having a cross-sectional area perpendicular to the longitudinal axis that differs from a cross-sectional area of the second portion perpendicular to the longitudinal axis,
   wherein:
      the distal end block is configured such that a position of a boundary between the second portion and the third portion corresponds to or substantially corresponds to an antinode of the ultrasonic vibration in a state in which the piezoelectric device generates the ultrasonic vibration, and the ultrasonic vibration is propagated to the proximal end block, the first portion, the second portion, and the third portion, and
      a resonance frequency of the ultrasonic vibration depends on a position of the boundary between the second portion and the third portion under a condition that a distance from the supported portion to a distal end of the third portion along the longitudinal axis is a predetermined length.

2. The ultrasound transducer according to claim 1, wherein
   the cross-sectional area of the second portion is smaller than the cross-sectional area of the third portion.

3. The ultrasound transducer according to claim 1, wherein
   the resonance frequency of vibration of the ultrasound transducer is lower when the position of the boundary is proximal of a predetermined reference position than when the position of the boundary is at the predetermined reference position, and
   the predetermined reference position is a position at which the resonance frequency of vibration of the ultrasound transducer is a predetermined resonance frequency.

4. The ultrasound transducer according to claim 1, wherein
   the cross-sectional area of the second portion is larger than the cross-sectional area of the third portion.

5. The ultrasound transducer according to claim 4, wherein
   the resonance frequency of vibration of the ultrasound transducer is higher when the position of the boundary is proximal of a predetermined reference position than when the position of the boundary is at the predetermined reference position, and
   the predetermined reference position is a position at which the resonance frequency of vibration of the ultrasound transducer is a predetermined resonance frequency.

6. The ultrasound transducer according to claim 1, wherein
   a cross-sectional shape of the second portion perpendicular to the longitudinal axis is uniform or substantially uniform along the longitudinal axis, and
   a cross-sectional shape of the third portion perpendicular to the longitudinal axis is uniform or substantially uniform along the longitudinal axis.

7. The ultrasound transducer according to claim 1, wherein
   the resonance frequency of vibration of the ultrasound transducer is higher when the position of the boundary is distal of a predetermined reference position than when the position of the boundary is at the predetermined reference position, and the predetermined reference position is a position at which the resonance frequency of vibration of the ultrasound transducer is a predetermined resonance frequency.

8. The ultrasound transducer according to claim 1, wherein the resonance frequency of vibration of the ultrasound transducer is lower when the position of the boundary is distal of a predetermined reference position than when the position of the boundary is at the predetermined reference position, and the predetermined reference position is a position at which the resonance frequency of vibration of the ultrasound transducer is a predetermined resonance frequency.

9. An ultrasound treatment system comprising:
an energy controller configured to output electric energy, and control output of the electric energy;
an ultrasound transducer that is connected to the energy controller, and configured to propagate ultrasonic vibration, the ultrasound transducer including:
a piezoelectric device configured to generate ultrasonic vibration from supplied electric energy along a longitudinal axis;
a proximal end block arranged on a proximal end side of the piezoelectric device along the longitudinal axis; and
a distal end block arranged on a distal end side of the piezoelectric device opposite to the proximal end side, the distal end block including, sequentially in a direction from a proximal end of the distal end block to a distal end of distal end block along the longitudinal axis:
a first portion adjacent to the piezoelectric device, the first portion including a supported portion;
a second portion adjacent to the first portion; and
a third portion adjacent to the second portion, the third portion having a cross-sectional area perpendicular to the longitudinal axis that differs from a cross-sectional area of the second portion perpendicular to the longitudinal axis; and
an ultrasound treatment tool that is connected to the ultrasound transducer, and configured to treat a subject with the ultrasonic vibration propagated from the ultrasound transducer,
wherein:
the distal end block is configured such that a position of a boundary between the second portion and the third portion corresponds to or substantially corresponds to an antinode of the ultrasonic vibration in a state in which the piezoelectric device generates the ultrasonic vibration, and the ultrasonic vibration is propagated to the proximal end block, the first portion, the second portion, and the third portion, and
a resonance frequency of the ultrasonic vibration depends on a position of the boundary between the second portion and the third portion under a condition that a distance from the supported portion to a distal end of the third portion along the longitudinal axis is a predetermined distance.

10. The ultrasound treatment system according to claim 9, wherein
the cross-sectional area of the second portion is smaller than the cross-sectional area of the third portion.

11. The ultrasound treatment system according to claim 9, wherein
the resonance frequency of vibration of the ultrasound transducer is lower when the position of the boundary is proximal of a predetermined reference position than when the position of the boundary is at the predetermined reference position, and the predetermined reference position is a position at which the resonance frequency of vibration of the ultrasound transducer is a predetermined resonance frequency.

12. The ultrasound treatment system according to claim 9, wherein
the cross-sectional area of the second portion is larger than the cross-sectional area of the third portion.

13. The ultrasound treatment system according to claim 12, wherein
the resonance frequency of vibration of the ultrasound transducer is higher when the position of the boundary is proximal of a predetermined reference position than when the position of the boundary is at the predetermined reference position, and the predetermined reference position is a position at which the resonance frequency of vibration of the ultrasound transducer is a predetermined resonance frequency.

14. The ultrasound treatment system according to claim 9, wherein:
a cross-sectional shape of the second portion perpendicular to the longitudinal axis is uniform or substantially uniform along the longitudinal axis, and
a cross-sectional shape of the third portion perpendicular to the longitudinal axis is uniform or substantially uniform along the longitudinal axis.

15. A method for manufacturing an ultrasound treatment tool, comprising:
assembling a distal end block that is configured to propagate ultrasonic vibration generated by an ultrasonic vibrator, the distal end block including sequentially in a direction from a proximal end to a distal end of the distal end block along a longitudinal axis:
a first portion adjacent to the ultrasonic vibrator, the first portion including a supported portion;
a second portion adjacent to the first portion; and
a third portion adjacent to the second portion, the third portion having a cross- sectional area perpendicular to the longitudinal axis different from a cross-sectional area perpendicular to the longitudinal axis of the second portion; and
determining a position at which a boundary between the second portion and the third portion corresponds to or substantially corresponds to an antinode of the ultrasonic vibration in a state in which the ultrasonic vibration is propagated at a predetermined resonance frequency as a reference position;
wherein a resonance frequency of the ultrasonic vibration differs according to the position of the boundary between the second portion and the third portion along the longitudinal axis relative to the reference position under a condition that a distance from the supported portion to a distal end of the third portion along the longitudinal axis is constant.

16. The method according to claim 15, wherein
the cross-sectional area of the second portion is smaller than the cross-sectional area of the third portion.

17. The method according to claim 15, wherein
the cross-sectional area of the second portion is larger than the cross-sectional area of the third portion.

18. The method according to claim 15, wherein
a cross-sectional shape of the second portion perpendicular to the longitudinal axis is uniform or substantially uniform along the longitudinal axis, and
a cross-sectional shape of the third portion perpendicular to the longitudinal axis is uniform or substantially uniform along the longitudinal axis.

19. The method according to claim 15, further comprising:
  adjusting the position of the boundary along the longitudinal axis relative to the reference position without changing a distance from the supported portion to a distal end of the third portion along the longitudinal axis to change a resonance frequency of vibration of the ultrasound treatment tool to be identical to or substantially identical to the predetermined resonance frequency.

20. The method according to claim 19, wherein
  the resonance frequency of vibration of the ultrasound treatment tool linearly or substantially linearly decreases as the position of the boundary between the second portion and the third portion is adjusted to move closer to the supported portion.

21. The method according to claim 19, wherein
  the resonance frequency of vibration of the ultrasound treatment tool linearly or substantially linearly increases as the position of the boundary between the second portion and the third portion is adjusted to move closer to the supported portion.

* * * * *